(12) United States Patent
Jean et al.

(10) Patent No.: US 12,048,798 B2
(45) Date of Patent: Jul. 30, 2024

(54) INTERFACE DEVICE FOR PERFORMING HEMODIALYSIS

(71) Applicant: UBIPLUG, Saint-Contest (FR)

(72) Inventors: Eric Jean, Bieville-Beuville (FR); Fabrice Missaire, Lillois (BE); Sylvain Thuaudet, Le Fresne-Camilly (FR)

(73) Assignee: UBIPLUG (FR)

( * ) Notice: Subject to any disclaimer, the term of this patent is extended or adjusted under 35 U.S.C. 154(b) by 1141 days.

(21) Appl. No.: 16/662,228

(22) Filed: Oct. 24, 2019

(65) Prior Publication Data

US 2020/0129689 A1 Apr. 30, 2020

(30) Foreign Application Priority Data

Oct. 26, 2018 (FR) ...................... 1859965

(51) Int. Cl.
*A61M 1/36* (2006.01)
*A61M 1/26* (2006.01)

(52) U.S. Cl.
CPC .......... *A61M 1/3661* (2014.02); *A61M 1/267* (2014.02); *A61M 1/3627* (2013.01); *A61M 1/3655* (2013.01); *A61M 1/3672* (2013.01)

(58) Field of Classification Search
CPC .. A61M 1/3653; A61M 1/3661; A61M 1/367; A61M 1/1565; A61M 1/267; A61M 1/3603; A61M 1/362265; A61M 1/3627; A61M 1/3646; A61M 1/3655; A61M 1/3672; A61M 2039/1022; A61M 2039/1027; A61M 2039/1061; A61M 2039/1066; A61M 2039/267; A61M 2205/3303; A61M 2205/3313; A61M 2205/3331; A61M 2205/3368; A61M 39/105; A61M 39/14; A61M 39/223; A61M 39/26; A61B 5/150992
See application file for complete search history.

(56) References Cited

U.S. PATENT DOCUMENTS

| | | | |
|---|---|---|---|
| 6,726,647 B1 * | 4/2004 | Sternby ................. | A61M 1/361 210/739 |
| 2005/0145549 A1 | 7/2005 | Jonsson et al. | |
| 2005/0205476 A1 * | 9/2005 | Chevallet .............. | A61M 1/308 210/257.2 |

(Continued)

FOREIGN PATENT DOCUMENTS

| | | |
|---|---|---|
| WO | 9964088 A1 | 12/1999 |
| WO | 2009001152 A1 | 12/2008 |

OTHER PUBLICATIONS

French Search Report for French Patent Application 1859965, mailing dated Jul. 10, 2019, 2 pages.

*Primary Examiner* — Dirk R Bass
(74) *Attorney, Agent, or Firm* — Lerner David LLP

(57) ABSTRACT

An interface device between a hemodialysis machine and venous and arterial tubes includes: a first port adapted to be connected to an output port of the hemodialysis machine and a venous port to inject blood into the venous tube. The interface device includes a second port adapted to be connected to an input port of the hemodialysis machine and an arterial port for receiving blood from the patient from the arterial tube. The interface device is further adapted to selectively allow or prohibit the passage of blood between the first and second ports and the venous and arterial ports respectively.

13 Claims, 12 Drawing Sheets

(56) References Cited

U.S. PATENT DOCUMENTS

2008/0177245 A1* 7/2008 Mesallum ............ A61M 1/367
　　　　　　　　　　　　　　　　　　　　604/500
2009/0173682 A1* 7/2009 Robinson ............... A61M 1/28
　　　　　　　　　　　　　　　　　　　　210/240
2013/0303986 A1　11/2013 Penalosa, Jr.

* cited by examiner

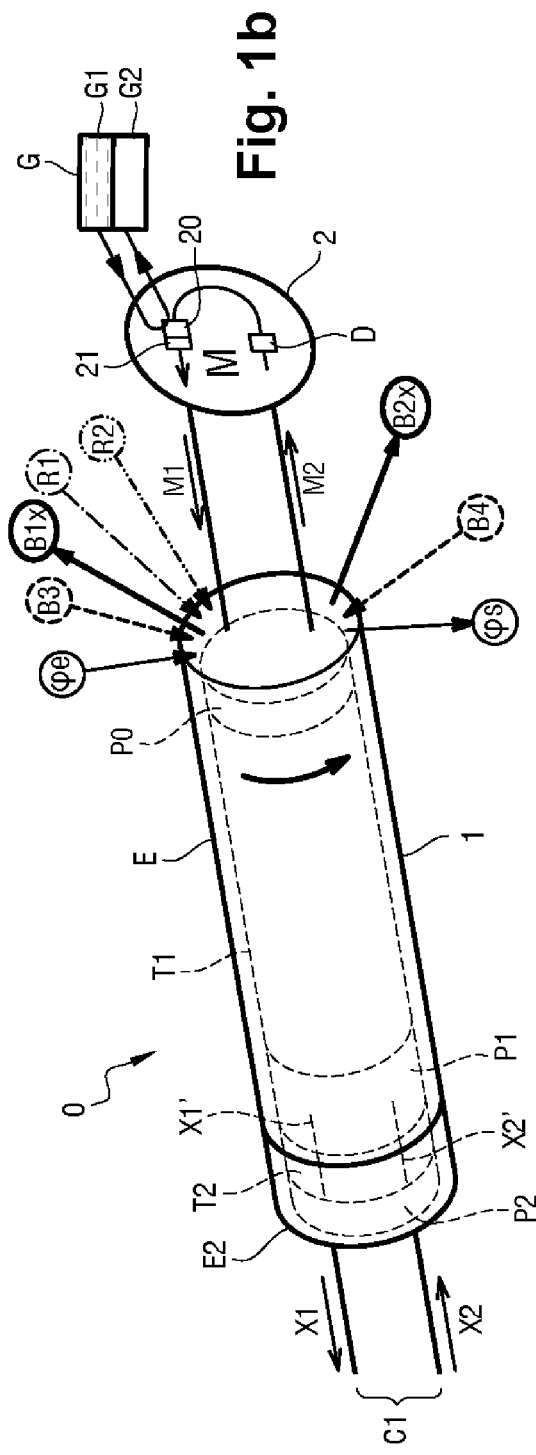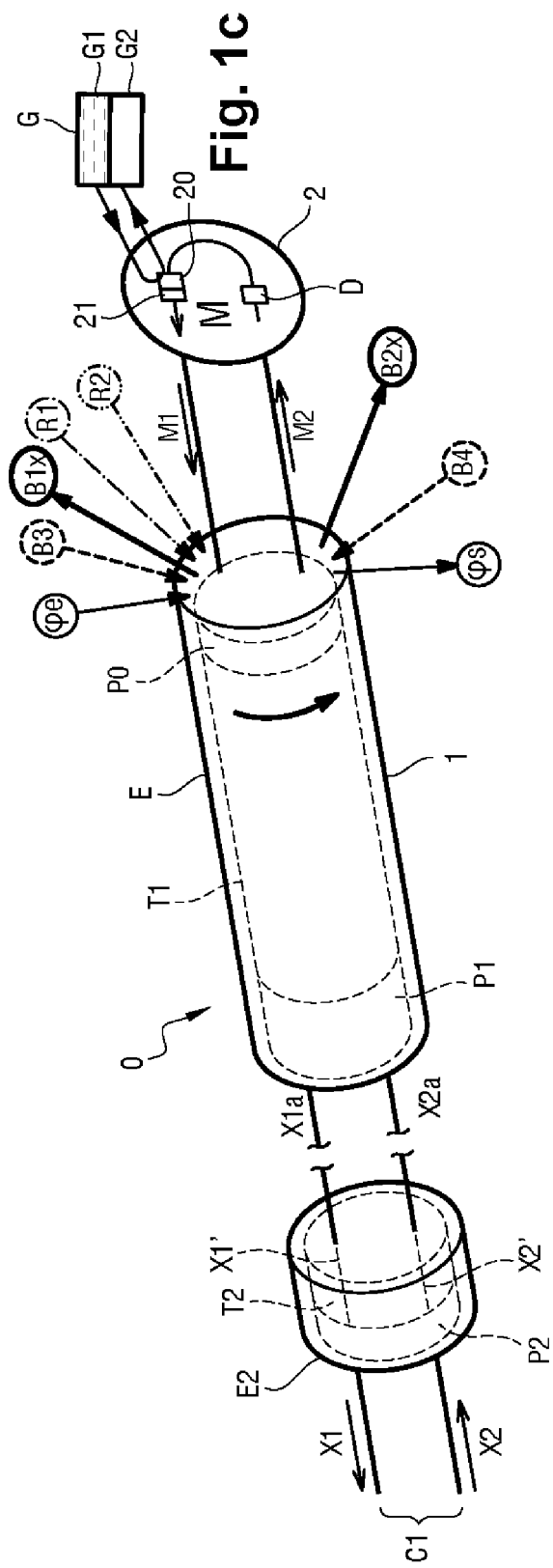

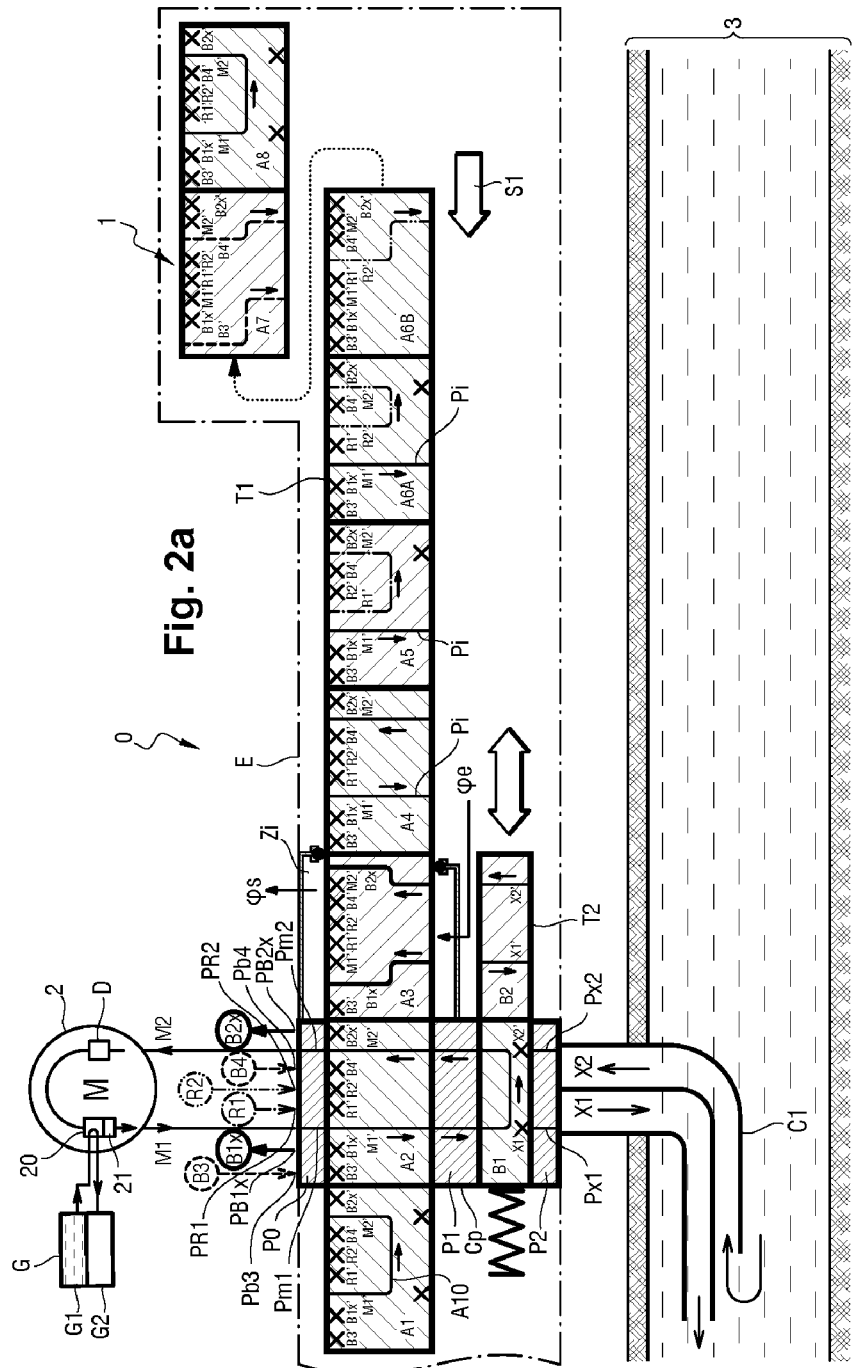

Operation

| Step 0 | Insertion of the catheter | |
|---|---|---|
| Step 1<br><br>A1B1 | Proximal line filling | 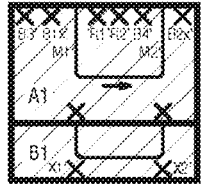 |
| Step 2<br><br>A2B1 | Intermediate line filling | 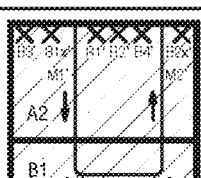 |
| Step 3<br><br>A3B2 | Opening of ports PX1 and PX2<br>Suction of locks | 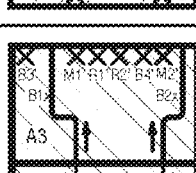 |
| Step 4<br><br><br><br>A4B2 | Blood circulation to machine 2<br>- Serum injection φ via PM1 + PX1<br>- Blood suction via PX2 + PM2<br>This step includes:<br>- Detection of blood supply by machine 2; then<br>- Start of dialysis at a rate by machine 2 (about 4 hours per dialysis session)<br>Stopping the machine | 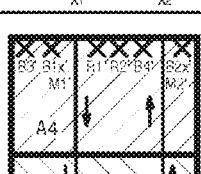 |
| Stage 5<br><br>A5B2 | Start of blood restitution by machine 2<br>(blood return via PR1 and injection via PX1) | 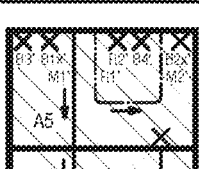 |

Fig. 3a

| | | | |
|---|---|---|---|
| Step 6A<br><br>A6AB2 | End of venous restitution by machine 2<br>Pushing of blood by serum injection φ via PR2 | | 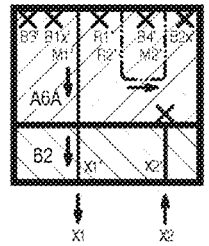 |
| Step 6B<br><br>A6BB2 | Arterial restitution step<br><br>Step 0<br>P1<br>Connection | | 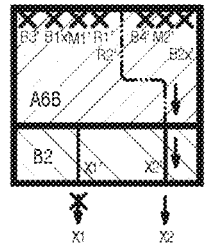 |
| Step 7<br><br>A7B2 | Injection of the locks<br>   - via B3 connected to PR1; and<br>   - via B4 connected to PR2<br>               Step 0<br>               P1<br>               Connection | | 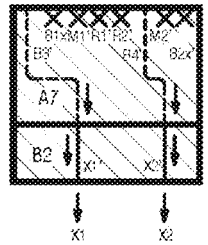 |
| Step 8<br><br>A8B1 | Closing of ports PX1 and PX2<br>Draining of proximal line | | 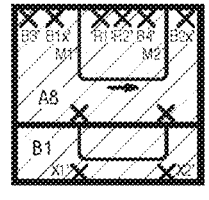 |

Fig. 3b

INTERFACE DEVICE FOR PERFORMING HEMODIALYSIS

CROSS-REFERENCE TO RELATED APPLICATIONS

The present application claims priority from French Patent Application No 18 59965 filed Oct. 26, 2018, the disclosure of which is hereby incorporated herein by reference.

The invention concerns the field of hemodialysis and in particular an interface device between a hemodialysis machine and tubes intended to be connected to a patient's circulatory system.

BACKGROUND OF THE INVENTION

Hemodialysis consists of the circulation of a patient's blood to a hemodialysis machine, then after processing the blood using the hemodialysis machine, the blood is returned to the patient's circulatory system.

The connection between the hemodialysis machine and the patient is made via at least one tube and via an interface device that serves as a removable connector between the hemodialysis machine and the tube. This tube has an end that opens into the circulatory system.

To implement this connection, the medical staff connects a first conduit to the hemodialysis machine and circulate a liquid through the first conduit to flush the gases out of it.

In parallel, the medical staff manually implants a catheter with the tube to connect it to the patient's circulatory system and then draws blood from the patient through the tube to fill it with blood and evacuate the gases.

Once the duct and catheter have been purged of their gases, the duct and catheter are then mechanically connected to each other via an interface device. The blood suction to the hemodialysis machine can then begin.

At the end of the hemodialysis session, the catheter connected to the patient is disconnected and saline is injected into it to return the blood in the catheter to the patient's circulatory system.

All these operations are repeated each time the patient is connected to the hemodialysis machine via a catheter. Thus, the implantation of a venous catheter to infuse blood into the patient and an arterial catheter to collect blood from the patient entails the repetition of manual operations. This increases the risk of contamination of the patient's circulatory system.

An interface device for performing hemodialysis is presented in the patent document U.S. Pat. No. 5,713,850A. This device allows fluid to be exchanged with the patient via a single tube connected to the patient.

It would therefore be useful to develop an interface device that minimizes the risk of contamination to the patient's circulatory system.

PURPOSE OF THE INVENTION

An object of this invention is to provide an interface device between a hemodialysis machine and at least one tube solving all or part of the above-mentioned disadvantages of the prior art.

SUMMARY OF THE INVENTION

To this end, according to the invention, an interface device is proposed between a hemodialysis machine and at least one venous tube intended to be connected to a patient's circulatory system in order to transfer blood from the hemodialysis machine to the circulatory system, this interface device comprising:
  a first port adapted to be connected to an output port of the hemodialysis machine;
  a venous port to inject blood into the venous tube;
  the interface device being adapted to selectively adopt a first configuration in which the passage of blood between the first port and the venous port is prohibited and a second configuration in which the first port is connected to the venous port to allow the passage of blood from the first port to the venous port.

The interface device according to the invention is essentially characterized in that it is also adapted to form an interface between the hemodialysis machine and an arterial tube intended to be connected to said patient's circulatory system to transfer blood from the circulatory system to the hemodialysis machine, this interface device also comprising:
  a second port adapted to be connected to an input port of the hemodialysis machine;
  an arterial port for receiving blood from the patient from the arterial tube, the interface device being further adapted to prohibit the passage of blood between the second port and the arterial port when the device is in its first configuration and to allow the passage of blood between the second port and the arterial port when the device is in its second configuration.

The interface device allows venous and arterial tubes to be connected to the same hemodialysis machine while allowing, using this single interface device, to:
  simultaneously prohibit the passage of fluid between the hemodialysis machine and the venous tube and between the hemodialysis machine and the arterial tube by placing the interface device in its first configuration;
  or simultaneously allow fluid to pass between the hemodialysis machine and the venous tube and between the hemodialysis machine and the arterial tube by placing the interface device in its second configuration.

Thus, with the same interface device, it is possible to selectively authorize or prohibit a venous fluid linking and an arterial fluid linking.

This greatly facilitates handling for the medical personnel while reducing the risk of handling errors.

For the purpose of understanding this invention, unless otherwise specified, any port of the interface device that is not explicitly mentioned as being connected to another port of the interface device shall be considered isolated from all other ports of the interface device.

In addition, when it is indicated that given ports are connected to each other, it means that there is a fluid communication between these given ports.

Similarly, when it is indicated that two given ports are isolated from each other, it means that there is no fluid communication between these given ports.

The fluid passing through the interface device is a liquid. For example, this fluid is blood, a dialysate, saline, or a liquid medication.

In another aspect, the invention concerns a hemodialysis system comprising a hemodialysis machine and an interface device according to any of the embodiments of the interface device described below.

In this hemodialysis system, the first port Pmt of the interface device is detachably connected to the output port of the hemodialysis machine and the second port of the interface device is detachably connected to the input port of the hemodialysis machine. The hemodialysis machine has a pump arranged to circulate fluids from its port of entry to its port of exit and the hemodialysis system also includes a venous tube and an arterial tube. The venous tube is connected to the venous port of the interface device. This venous tube is intended to be connected to a patient's circulatory system to transfer blood from the hemodialysis machine to the circulatory system via the interface device. The arterial tube is connected to the arterial port of the interface device. This arterial tube is intended to be connected to the patient's circulatory system to transfer blood from the circulatory system to the hemodialysis machine via the interface device.

The hemodialysis system according to the invention is advantageous at least for the reasons stated above with reference to the interface device according to the invention.

BRIEF DESCRIPTION OF THE DRAWINGS

Other characteristics and advantages of the invention will be readily apparent from the following detailed description, given by way of non limiting examples, while referring to the appended drawings, wherein:

FIG. 1b illustrates a system identical to that of FIG. 1a, the only difference being that the interface device 1 is distributed in two enclosures E and E2 mechanically assembled together, in a detachable manner, this mode of construction making it possible to have a one-piece and rigid interface device when the chambers are assembled together while allowing the mechanical connection between the tubes X1, X2 and the ports M1, M2 of the hemodialysis machine to be interrupted by separating the interface device into two parts respectively contained in the separate chambers E and E2;

FIG. 1c illustrates a system identical to that of FIG. 1b, the only difference being that the interface device 1 is divided here into two chambers E and E2 which are connected to each other by an intermediate venous tube X1a and an intermediate arterial tube X2a which are deformable, the enclosures E, E2 being here far from each other; this embodiment makes it possible to have an interface device in two rigid blocks and separated from each other by flexible tubes X1a, X2a whose length can vary as needed, this embodiment allowing the mechanical connection between tubes X1, X2 and ports M1, M2 of the hemodialysis machine to be interrupted by detaching the intermediate tubes from one of the enclosures E or E2, the respective fluid connections between ports M1, M2 and the venous and arterial tubes X1, X2 can be interrupted either by actuating a first drawer of the interface device placed in the first enclosure E or by actuating a second drawer of the interface device placed in the second enclosure E2, so there is a fluid connection interruption function which is redundant and distributed in separate enclosures;

FIG. 2a shows an embodiment of system 0 with an interface device 1 according to the invention integrated in a single enclosure as shown in FIG. 1a;

FIGS. 3a and 3b describe a succession of steps with configurations taken by the interface device according to the invention

DETAILED DESCRIPTION OF THE INVENTION

Figure 1A:
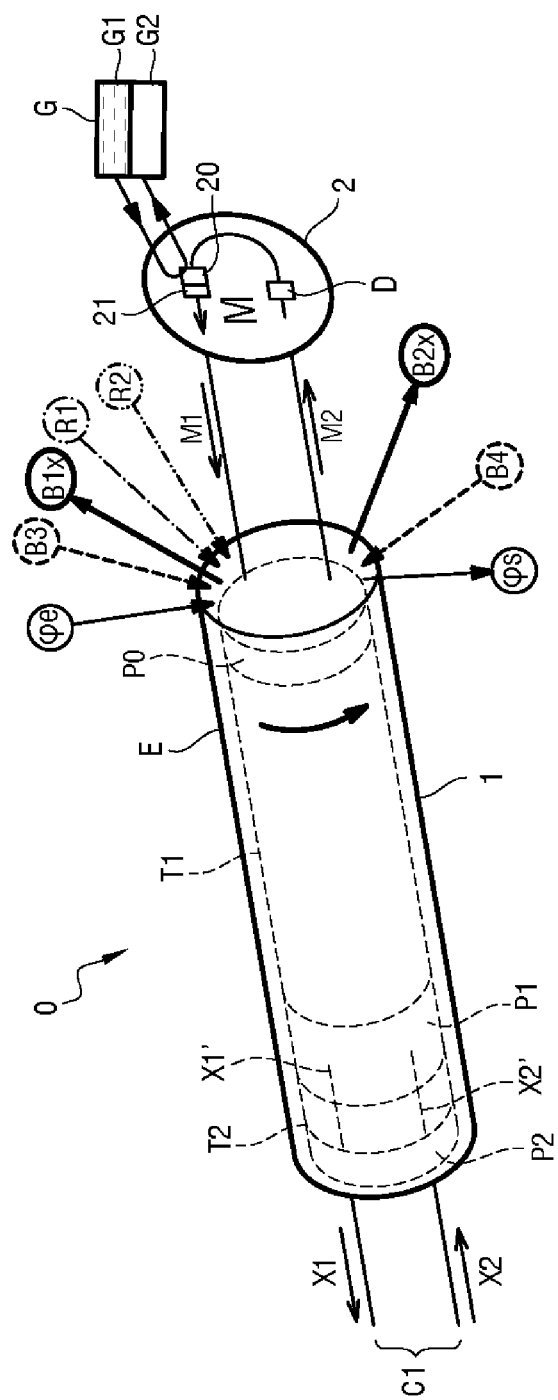
FIG. 1a shows a hemodialysis system 0 according to the invention comprising a hemodialysis machine 2, an interface device 1 according to the invention and venous and arterial tubes X1, X2, this interface device 1 being contained in a single enclosure E and attached to venous and arterial tubes X1, X2 and to entry and exit ports M1, M2 of the machine to selectively allow or prohibit fluid connections between the port of the machine M1 and the tube X1 and between the port M2 and the tube X2.

According to a general aspect, the invention concerns a hemodialysis system 0 illustrated through FIGS. 1a to 2c and through FIGS. 4a to 4j. This system 0 includes a hemodialysis machine 2, an interface device 1 and venous and arterial tubes X1, X2. These tubes X1, X2 are each designed to be fluidically connected to a patient's circulatory system 3. These venous and arterial tubes X1 and X2 belong preferably to the same catheter C1.

Each of the tubes X1, X2 is preferably formed of a flexible conduit, for example thermoplastic, compatible with medical use (polyurethane, PEEK, silicone or other), to facilitate its handling and its path between the circulatory system 3 and the interface device 1.

The venous tube X1 is essentially intended for the injection of fluid from machine 2 to the patient, and the arterial tube X2 is essentially intended for the sampling (aspiration) of fluid from the patient to the hemodialysis machine 2.

The tubes are connected to the circulatory system 3 either via an arterio-venous fistula, via a central catheter tunnelled in the patient (a tunnelled central catheter is a catheter remaining in place in the patient's body between two hemodialysis sessions) or via an implantation of a non-tunnelled hemodialysis catheter (these tubes can belong to one or more catheters). More precisely, the interface device 1 according to the invention forms:

an interface between the hemodialysis machine 2 and an arterial tube X2 to be connected to said patient's circulatory system 3 to transfer blood from the circulatory system 3 to the hemodialysis machine 2; and an interface between the hemodialysis machine 2 and at least one venous tube X1 to transfer blood from the hemodialysis machine to the circulatory system 3. Said interface device 1 comprises:

a first port Pmt adapted to be connected, preferably removably via a first connection, to an output port M1 of the hemodialysis machine 2; and a second port Pm2 adapted to be connected, preferably in a removable manner via a second connection possibly fixed to said first connection, to an input port M2 of the hemodialysis machine;

a venous port Px1 for injecting blood into the venous tube X1, this venous port Px1 being preferably removably attached, via a connector, to the venous tube X1; and an arterial port Px2 to receive (to circulate, e.g. by aspiration) blood from the patient's arterial tube X2, this arterial port Px2 being preferably removably attached, via a connection, to the arterial tube X2.

The second port Pm2 of interface device 1 is suitable for transferring blood from interface device 1 to an input port M2 of the hemodialysis machine 2.

The hemodialysis machine has a pump M arranged to pump/circulate fluids from its input port M2 to its output port M1.

The first port Pm1 of the interface device 1 is adapted to receive blood from the output port M1 and transfer it to the venous tube X1.

The hemodialysis machine 2 is also adapted to carry out exchanges between the fluid it transfers, in this case the patient's blood, and a liquid dialysate to allow purification of the fluid (blood). For this purpose, the hemodialysis machine has an internal circuit connected on one side to the input port M2 and on the other side to the output port M1.

The pump M of the hemodialysis machine is preferably a peristaltic pump, to transfer fluid from the input port M2 to the output port M1 at a precisely controlled flow rate.

This internal circuit of the hemodialysis machine preferably includes at least one semi-permeable membrane 20 allowing exchanges between the fluid/blood and the chemically formulated dialysate and/or filters to purify the fluid/blood.

Preferably, this semi-permeable membrane 20 allows exchanges between a circuit through which the patient's blood passes and a dialysate circuit. The dialysate circuit extends from a previously formulated reserve of dialysate G1 to a reserve of used dialysate G2 via a contact zone against the semi-permeable membrane 20 to carry out exchanges with the patient's blood.

The flow rate and quality of this dialysate can be controlled by means of a dialysate pump and/or dialysate analysis valves and/or sensors and/or semi-permeable membrane functioning analysis sensors 20 and/or dialysate pressure sensors and/or quantity sensors of the dialysate remaining in the reserve G1 and/or quantity sensors of the used dialysate present in the reserve G2.

The hemodialysis machine 2 also includes a debubblizer D to remove gas bubbles contained in the fluid transferred via the hemodialysis machine 2. Here, debubblizer D is connected in series between the input and output ports M2, M1 and is preferably located between the port M2 and the membrane. If necessary, the machine can be equipped with other debubblizers to ensure that no liquid containing bubbles is dispensed to the patient.

The hemodialysis machine may also include a detection device 21 for detecting bubbles and/or impurities and/or a fluid flow between its input and output ports M2, M1 and/or a pressure of the fluid passing through machine 2 and/or a dialysate level in a dialysate reserve connected to machine 2 to bring this dialysate into contact with the semi-permeable membrane.

This detection device 21 is connected to an electronic control unit of the hemodialysis machine 2 to control the operation of the pump M according to measurements made by this detection device 21.

This electronic unit can also be connected to at least some of said dialysate circuit sensors and dialysate circuit actuators for example to control dialysate flows in the dialysate circuit, dialysate dosages with other components.

This electronic unit can also be connected to one or more semi-permeable membrane state sensors to control the operating parameters of the various actuators, including the pump M, according to measurements made with this/these state sensor(s).

The hemodialysis machine may also include a communication interface adapted to detect a current configuration of the interface device 1 according to the invention in order to adjust the operation of the hemodialysis machine according to the current configuration of the interface device 1 thus detected. This communication interface may include a detachable connection between the hemodialysis machine 2 and the interface device 1.

This communication interface can be adapted to transmit:

from interface device 1 to hemodialysis machine 2 a signal of current configuration of interface device 1 representative of a current configuration adopted by this interface device 1; and/or from the hemodialysis machine 2 to the interface device 1, a configuration change signal, the interface device 1 including an actuator, for example a motor, controlling the configuration change of the interface device 1 according to the configuration change signal received by the interface device 1 so as to switch the interface device from a current configuration to another selected configuration in a succession of predefined configurations. The different configurations selectively adopted by the interface device will be presented below.

FIGS. 3a and 3b illustrate a succession of configurations that can be selectively adopted by the interface device (by selectively, it is meant that the interface device can only adopt one of the listed configurations at any given time).

To illustrate these different configurations, two drawers T1, T2 are represented, each of these drawers T1, T2 being movable by sliding against two corresponding bodies between which it sealingly slides. Here, the interface device has several drawers and several bodies P0, P1, P2 and possibly P3.

The first drawer T1 sealingly slides between a base body P0 and an intermediate body P1. This base body P0 carries said first port Pm1 and second port Pmt as well as other ports of the interface device which will be presented below under the names of third port Pb1x, fourth port Pb2x, fifth port Pb3, sixth port Pb4, start of release port Pr1, release port Pr2.

The second drawer T2 sealingly slides between two bodies, one of which is a patient body P2 carrying the venous and arterial ports Px1, Px2 and the other body is either said intermediate body P1, or another intermediate body P3 (in the case where the device is distributed in at least two enclosures E, E2).

Figure 2B:
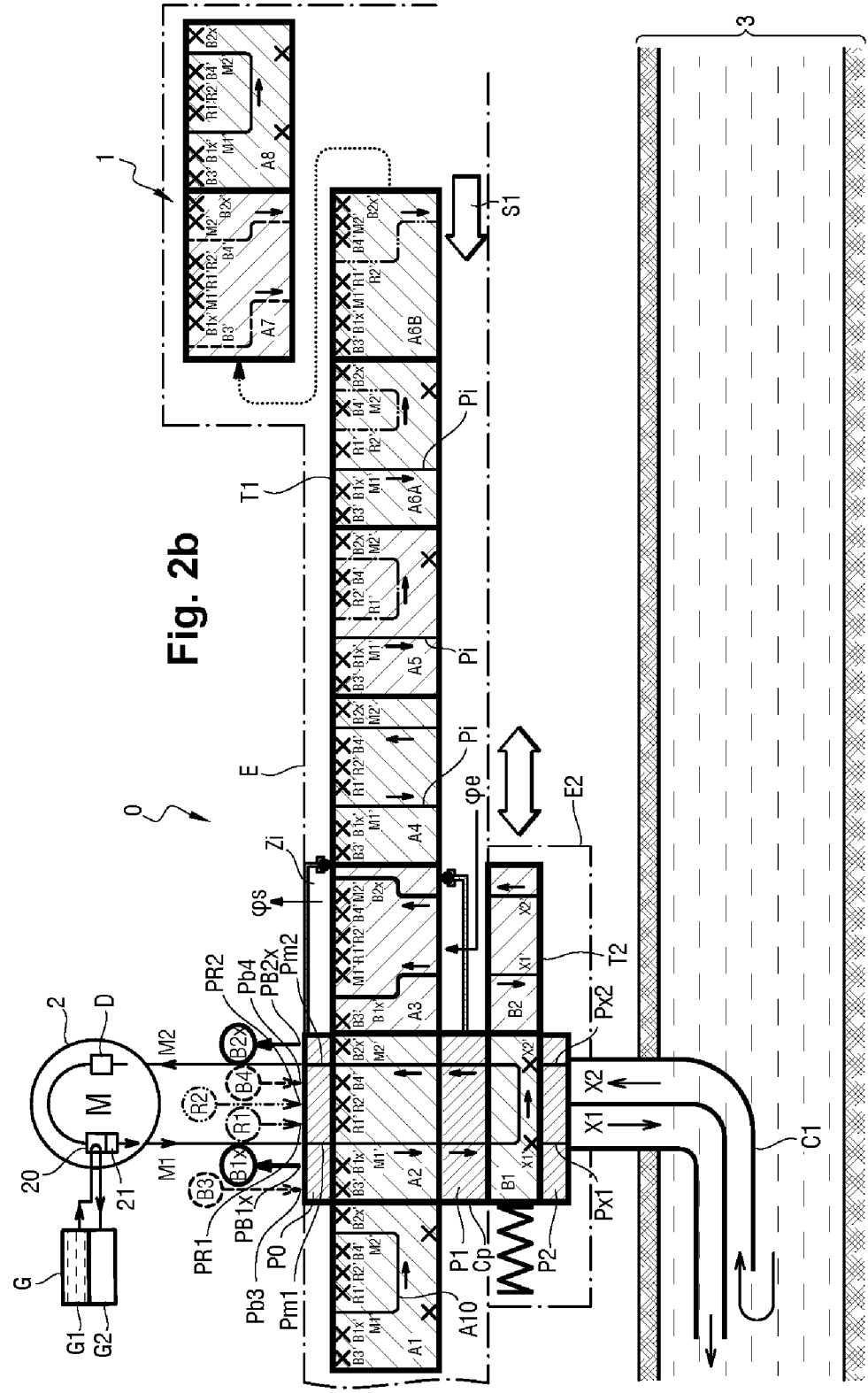
FIG. 2b shows an embodiment of system 0 with an interface device 1 according to the invention distributed in two separate enclosures E, E2 and mechanically assembled to each other in a detachable manner as shown in FIG. 1b.

In applications where the interface device 1 is contained in a single enclosure E, as in FIG. 2a, or in two adjacent enclosures E, E2 rigidly joined together, as in FIG. 2b, it is preferred to use a single intermediate body P1 against which the two drawers T1, T2 slide sealingly.

This intermediate body P1 is crossed by conduits to allow the passage of fluid between internal circuits Pi at the first drawer T1, and internal circuits at the second drawer T2.

Figure 2C:
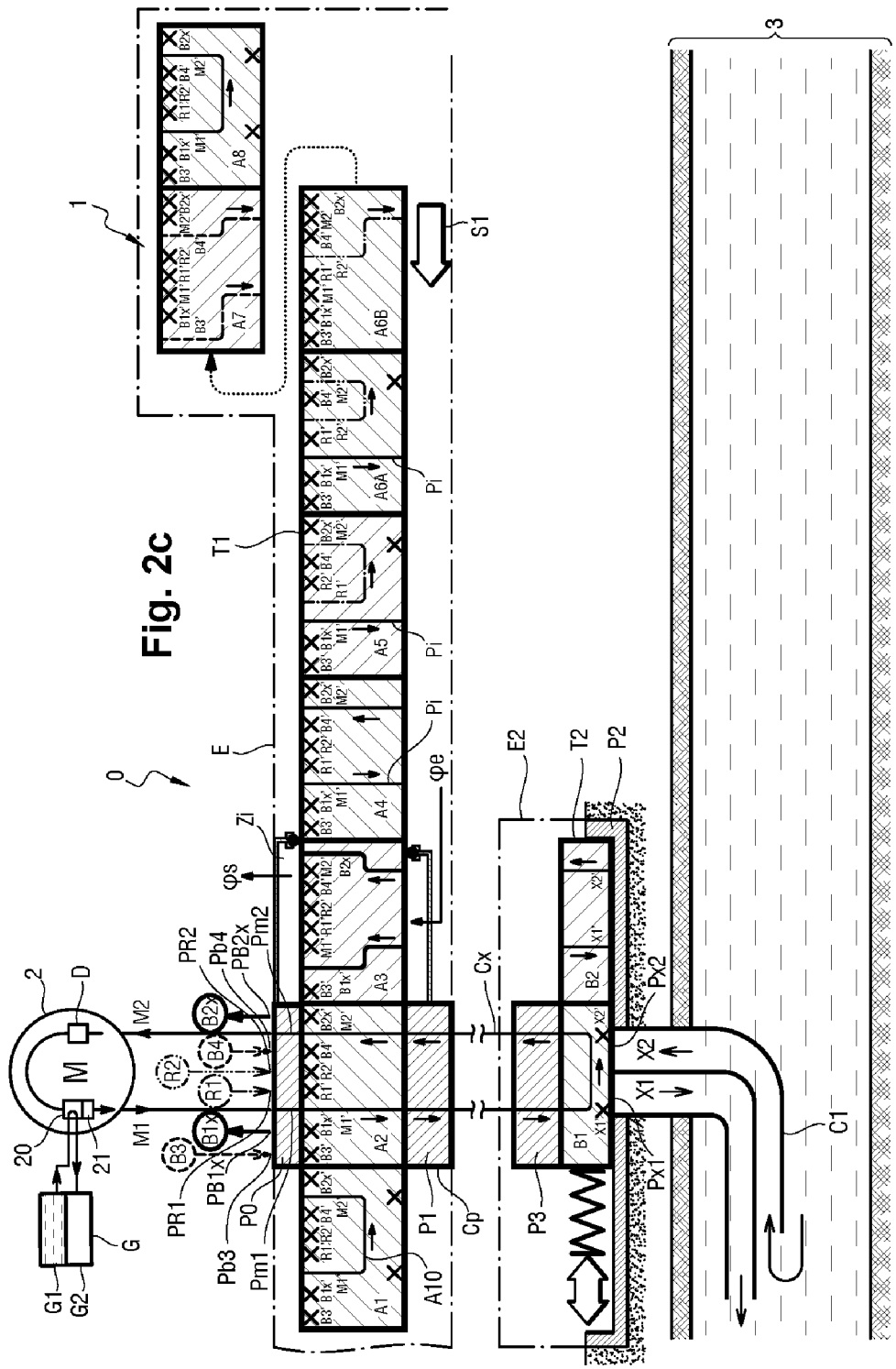
FIG. 2c shows an embodiment of system 0 with an interface device 1 according to the invention distributed in two separate enclosures E, E2 connected to each other via flexible intermediate tubes X1a, X2a as in FIG. 1c.
Figure 4A:
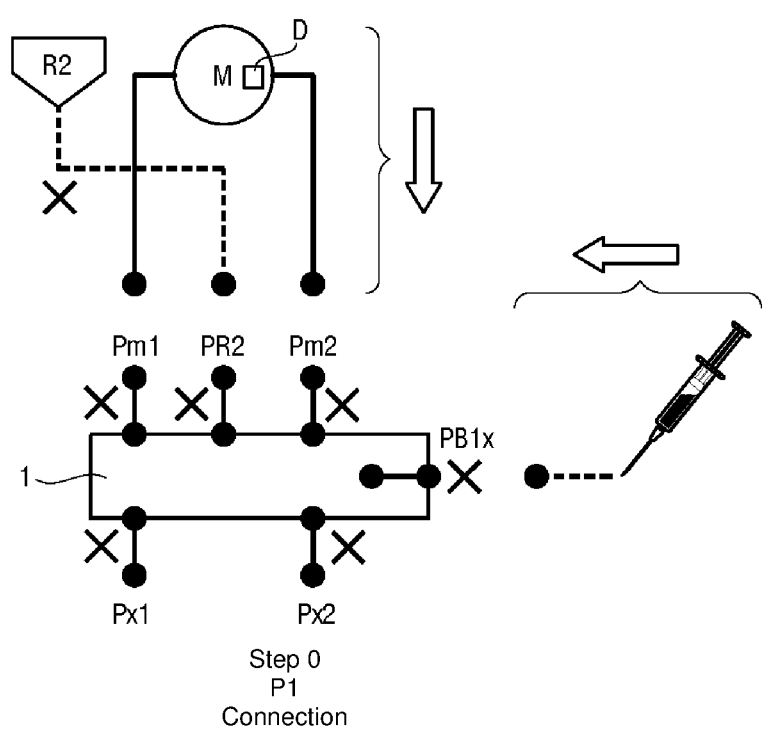
FIGS. 4a, 4b, 4c, 4d, 4e, 4f, 4g, 4h, 4i, 4j illustrate the different operating steps Step0, Step1, Step2, Step3a, Step3b, Step4, Step5, Step6B, Step7A, Step7b, Step8 respectively, of an interface device 1 according to the invention (this interface device 1 of FIGS. 4a to 4j is easier to manufacture because it has a reduced number of ports and positions/configurations compared to that of FIGS. 2a to 2c).
Figure 4B:
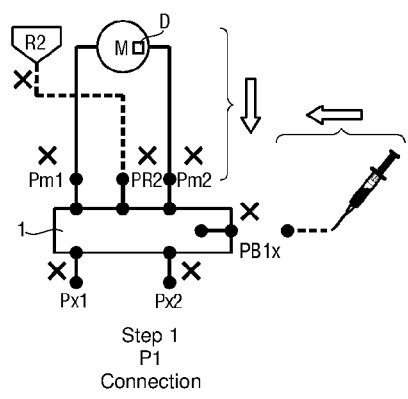
Figure 4C:
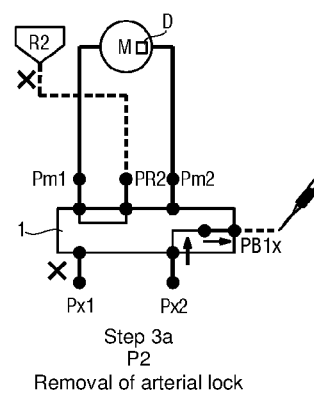
Figure 4D:
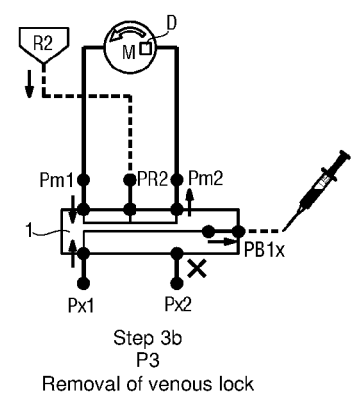
Figure 4E:
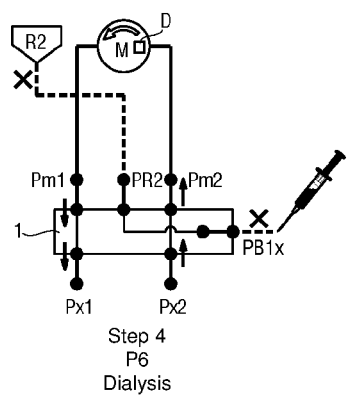
Figure 4F:
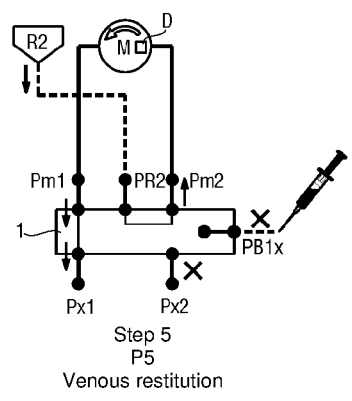
Figure 4G:
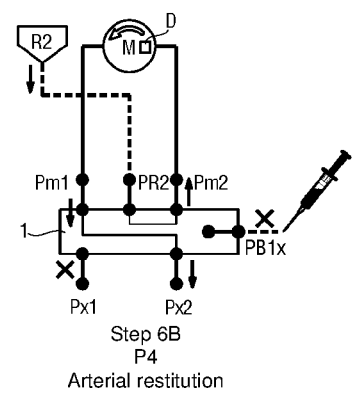
Figure 4H:
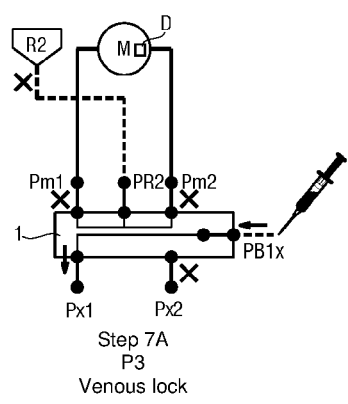
Figure 4I:
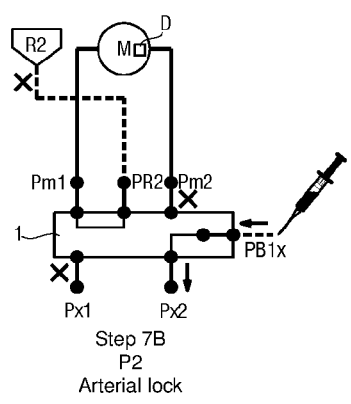
Figure 4J:
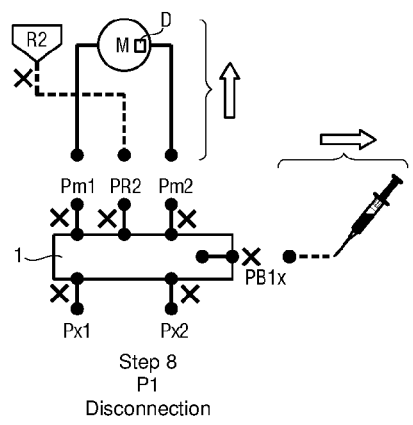

In other embodiments, such as that in FIG. 2c, where it is desired that the interface device 1 has two parts that move relative to each other, then the interface device 1 has two enclosures E, E2. The first enclosure E contains the basic body P0, an intermediate body P1 and the first drawer T1 while the second enclosure E2 contains another intermediate body P3, the patient body P2 and the second drawer T2.

The first drawer T1 is located in the first enclosure E where it is sealingly slidably mounted between the base body P0 and the first intermediate body P1, while the second drawer T2 is located in the second enclosure E2 where it is sealingly slidably mounted between the patient body P2 and the second intermediate body P3, the first and second intermediate bodies P1, P3 being fluidly connected together by flexible tubes Cx. It can be ensured that each flexible tube Cx has one end connected, possibly detachably, to the first intermediate body P1 and a second end connected, possibly detachably, to the second intermediate body P3.

In each of the embodiments of FIGS. 2a to 2c, the drawers T1, T2 and the bodies P0, P1, P2, P3 are designed in such a way that, depending on the respective positions of the drawers T1, T2 in relation to the bodies, there are authorisations and/or prohibitions for fluid passage between ports Pb1x, Pb2x, Pb3, Pb4, Pr1, Pr2, Px1, Px2 carried by the bodies P1, P2 in accordance with the given configurations of device 1.

For this purpose, each drawer T1, T2 has several cells, in this case cells A1, A2, A3, A4, A5, A6A, A6B, A7, A8 for the first drawer T1 and cells B1, B2 for the second drawer T2. The number and configurations of these cells can vary depending on the configurations to be implemented.

Each given configuration of the device is thus defined by a given sliding position of the first drawer T1 and a given sliding position of the second drawer T2.

As shown in FIG. 3, the interface device is adapted to selectively adopt a first A1B1 (step 1) and second A4B2 (step 4) configuration.

In its first configuration A1B1:
the passage of blood between the first port Pm1 and the venous port Px1 is prohibited; and
the passage of blood between the second port Pm2 and the arterial port Px2 is prohibited.

This first configuration is useful at least to isolate the machine 2 from the patient's circulatory system.

In its second configuration A4B2 (step 4), the first port Pm1, is connected to the venous port Px1 to allow blood to pass from the first port Pm1 to the venous port Px1, the second port Pm2 and the arterial port Px2 are also connected together to allow blood to pass from the arterial port Px2 to the second port Pm2. In this second configuration, only ports Pm1, Px1, Pm2, Px2 are open and the other ports of the device are closed.

This second configuration A4B2 is useful for circulating blood in a loop through the circulatory system 3, arterial tube X2, arterial port Px2, second port Pm2, entry port M2, hemodialysis machine 2 and its internal circuit, exit port M1, second port Pm1, venous port Px1, venous tube X1 and finally the circulatory system 3.

One of the advantages of the Interface Device 1 according to the invention, is that it allows switching from one configuration to another without having to manually disconnect a port from the machine. This allows or interrupts the flow of fluid between the tubes X1, X2 and the hemodialysis machine while limiting the risk of patient contamination.

Preferably, the interface device is arranged so that when in its first configuration A1B1, the first port Pm1 and the second port Pm2 are then connected via an internal circuit A10 to the interface device 1.

Preferably, the interface device is arranged so that when in its second configuration A4B2, communication between the first port Pm1 and the second port Pm2 via this internal circuit A10 is then prohibited.

Thus, in the first configuration, it is possible to connect the first and second ports Pm1 and Pm2 of device 1 via an internal circuit A10 which allows to connect the output port M1 and the input port M2 while isolating these ports M1, M2 from the arterial and venous tubes X2, X1.

This first configuration allows the hemodialysis machine to be isolated from the patient's circulatory system 3 while allowing the liquid fluid to circulate through the hemodialysis machine. Gases in the hemodialysis machine circuit can be evacuated and replaced by liquid passing through the internal circuit A10 of the interface device. This operation of filling the hemodialysis machine 2, interface device 1 and the circuits that extend between the hemodialysis machine 2 and interface device 1 with liquid is performed without having to disconnect the input and output ports M1, M2.

As shown in different FIGS. 1a to 2c, device 1 also has a third port Pb1x and this interface device 2 is adapted to selectively adopt an unlocking configuration A3B2 distinct from said first A1B1 and second A4B2 configurations.

In this unlocking configuration A3B2 Step3a, the third port Pb1x is connected to only one of said venous port Px1 or arterial port Px2 while the first port Pm1 and the second port Pmt are isolated from the venous port Px1 and the arterial port Px2 respectively, these venous and arterial ports also being isolated from each other.

By ports isolated from each other, isolated one from the other, it is meant that these ports do not communicate fluidly with each other.

This unlocking configuration A3B2 allows the suction of a locking fluid present in the venous tube X1 and/or the arterial tube X2 to be released and to allow the passage of blood/circulation of liquid fluid. A locking fluid is a substance with an anticoagulant function and a buffer function to prevent blood from passing through the tube containing it. Possibly, the locking fluid may have an antiseptic function.

Typically, after hemodialysis, locking fluid is injected into each tube remaining in the patient until the next hemodialysis session. This locking fluid prevents the tube from clogging and precludes the need to replace it.

With interface device 1, locking fluid can be injected or sucked into the venous tube X1 and/or arterial tube X2 while leaving the tube(s) connected to interface device 1. Again, this reduces the need for handling fittings and ports, and the associated risks to the patient.

In order to draw locking fluid from the venous tube X1, the system according to the invention can also include a venous syringe B1x for aspirating locking fluid connected to the third port Pb1x.

In the embodiment presented in FIGS. 4a to 4j, it can be seen that the third port Px1 is intended to be connected either to the venous port Px1, the arterial port Px2 or possibly to a return port Pr2 intended to inject a fluid to be returned to the patient (for example, physiological saline solution or liquid medication). Thus, this same third port Px1 can be used with either venous port Px1 or arterial port Px2 to insert a lock or aspirate it. For this purpose, this third port is designed to be connected successively to a suction syringe or a locking fluid injection syringe. The coupling of each syringe is done manually by the hemodialysis practitioner.

This solution is also advantageous since it allows venous or arterial port locking operations to be performed using this single third port Pb1x.

To perform venous or arterial locking, the interface device is simply placed in the unlocking configuration and an arterial or venous lock is injected via that of ports Px1 or Px2 which is connected to the third port Pb1x.

Alternatively, as shown in FIGS. 2a to 2c, interface device 1 may also have a fourth port Pb2x, this interface device being further arranged so that when in its unlocking configuration A3B2, the fourth port Pb2x is then connected to one of said venous Px1 or arterial Px2 ports which is not connected to said third port Pb1x, this fourth port Pb2x being isolated from the other ports of device 1.

Preferably, in this unlocking configuration A3B2, the third and fourth ports Pb1x, Pb2x are isolated from each other to allow locking fluid to be drawn into the venous tube X1 via the third port Pb1x and locking fluid into the arterial tube X2 via the fourth port Pb2x. This suction can be done using a first suction means connected to only the third port Pb1x and a second suction means connected to only the fourth port Pb2x.

For this purpose, the system according to the invention may include an arterial syringe B2x for suction of locking fluid connected to the fourth port Pb2x to be able to draw locking fluid from the arterial tube X2.

This results in separate suction circuits/suction means which limit the risk that an operation of locking fluid suction in the venous tube or arterial tube will interfere with an operation of locking fluid suction in the other of these tubes.

According to a preferred embodiment, interface device 1 also has a fifth port Pb3, the interface device being adapted to selectively adopt a locking configuration A7B2 (step7) distinct from said first, second and unlocking configurations A1B1, A4B2, A3B2. In this locking configuration A7B2, the fifth port Pb3 is connected to said venous port Px1 while the first port Pmt, the second port Pmt, the third port Pb1x, the venous port Px1 and the arterial port Px2 are isolated from each other.

In this locking configuration A7B2, the fourth port Pb2x and the fifth port Pb3 are also isolated from each other.

In this locking configuration, this fifth port Pb3 is connected to the venous port Px1 while being isolated from all other ports of the device.

This locking configuration allows the injection, via the fifth port Pb3, of a locking fluid into the venous tube X1 to prevent the presence of blood in this venous tube X1.

This limits the risk of clogging this venous tube X1 with coagulated blood between two successive hemodialysis sessions.

To this end, the system according to the invention may include a venous syringe B3 for injecting locking fluid connected to the fifth port Pb3 to be able to inject locking fluid into the venous tube X1.

According to a preferred embodiment of the invention, interface device 1 also has a sixth port Pb4, the interface device 1 being also adapted, in its locking configuration A7B2, for the sixth port Pb4 to be connected to said arterial port Px2 while being isolated from all the other ports of the device.

The interface device according to the invention thus makes it possible to carry out the operations of removal or inserting of locking fluid in the venous tube X1 and the arterial tube X2 while leaving the hemodialysis machine 2 and the venous and arterial tubes X1, X2 connected to the concerned ports of the interface device. Once again, this limits the risk of contamination of the circulatory system by connecting or disconnecting ports.

To this end, the system according to the invention may include an arterial syringe B4 for injecting locking fluid connected to the sixth port Pb4, to be able to inject locking fluid into the arterial tube X2.

According to a preferred embodiment, the interface device also has a release port Pr2 and the interface device 1 is further adapted to selectively adopt a venous release configuration A6aB2 distinct from other configurations that can be adopted by the device: A1B1, A4B2, A3B2, A7B2.

In this venous release configuration A6aB2, the release port Pr2 is connected to said second port Pmt to be able to inject a release fluid into the hemodialysis machine 2, the first port Pm1 being then connected to said venous port Px1 and isolated from all other ports of the interface device, and the arterial port Px2 being at least isolated from the venous port Px1, the first port Pm1 and the second port Pm2.

In this venous release configuration A6aB2, the device allows a fluid to be released (release fluid) to pass through only the second port Pm2 of the hemodialysis machine while allowing the hemodialysis machine to inject fluid into the venous tube X1 via the output port M1 connected to the first port Pm1 and the venous port Px1.

To this end, the system according to the invention may include a reserve R2 of fluid to be released (e.g. a reserve of saline solution, dialysate, liquid medication) connected to the release port Pr2 to be able to inject fluid to be released to the interface device when the interface device is in its venous release configuration A6aB2, Step5.

Since the hemodialysis machine 2 forms a circuit extending between its input port M2 and its output port M1, the hemodialysis machine pumps the release fluid from its input port M21 to its output port M1 to push the blood contained in the machine and release it to the patient's venous tube X1 and then to the patient's circulatory system 3.

Thus, the volume of blood contained in the hemodialysis machine 2, in the venous tube X1 and in the pipes connecting the hemodialysis machine 2 to the interface device 1 can be returned to the patient. This is particularly important to limit the amount of blood lost by the patient during hemodialysis.

According to a preferred embodiment, device 1 is further adapted to selectively adopt an arterial restitution configuration A6bB2, Step6B, distinct from other configurations that may be adopted by the interface device: A1B1, A4B2, A3B2, A7B2, Step1, Step4, Step5.

In this arterial release configuration A6bB2 (see FIGS. 2a to 2c and FIG. 3), the release port Pr2 can be connected to said arterial port Px2 to inject release fluid into the arterial tube X2, the other ports of the device then being isolated from each other.

Alternatively, the interface device can be adapted so that in its arterial delivery configuration Step6B (see FIG. 4g), the delivery port Pr2 is connected to the second port Pm2 of the hemodialysis machine while the first port Pm1 of the machine is connected to said arterial port Px2.

In this arterial release configuration A6bB2, Step6B, either the release fluid flows directly from the release port Pr2 to the arterial port without going through/back through the machine, or the release fluid flows from the release port Pr2 to the second port Pm2, then this release fluid passes through the machine M and its debubblizer D to exit and pass from the first port Pm1 to the arterial port Px2 (the interface device 1 in arterial release configuration connects its ports Pm1 and Px2 to one another by isolating them from the other ports of the interface device).

In an embodiment not illustrated, it is also possible that in the release configuration the two venous and arterial ports are connected to the release port Pr2 or possibly to the first port Pm1 to simultaneously perform the release. This solution saves time during release but has the disadvantage of not controlling the volume of fluid returned to each tube X1, X2.

As mentioned above, this release fluid may be a saline.

In this arterial release configuration A6bB2, the device allows a fluid to be released from the release port Pr2 to the arterial port Px2 while isolating the other ports from each other, thus allowing the arterial tube X2 to be filled with fluid to be released and the blood present in this tube to be pushed into the circulation system 3.

This blood release limits blood loss during hemodialysis and avoids the risk of clogging the arterial tube X2.

In a particular embodiment, the interface device can be adapted so that when it is in its first configuration Step1, its return port Pr2 is then connected to at least one of said first port Pm1 and second port Pm2.

Thus, the first and second ports Pm1, Pm2 can be degassed by injecting a fluid (liquid) via the return port Pr2.

Preferably, interface device 1 also has a control mechanism arranged to be moved in a first direction S1 with respect to enclosure E of interface device 1. This movement makes it possible to control a change in the configuration of the interface device and, for example, its transition from its first configuration A1B1 to its second configuration A4B2.

In other words, the control mechanism controls the transition from a current configuration in which the device is located to another configuration of the selected device, this other configuration being selected from the different configurations that the device can selectively adopt.

The sequence of the different configurations required for completing a hemodialysis will be detailed below. Ideally, the control mechanism moves only in the direction S1 so the device can only pass once in a given configuration.

Preferably, the interface device has a physiological liquid supply port φe (a physiological liquid is for example physiological serum, a dialysate or pure water) to an internal zone Zi of the interface device and a physiological liquid discharge port φs outside this internal zone of the interface device 1.

The interface device comprises a plurality of portions of internal circuits Pi to the interface device, each of these portions of internal circuits being arranged to be selectively either connected between the physiological liquid supply port φe and the physiological liquid discharge port φs, or connected to at least one of said venous or arterial ports Px1, Px2.

Each portion of the internal circuits Pi can thus be filled with physiological fluid before being connected to one of the venous port Px1 or arterial port Px2.

This limits the risk of gas migration from a portion Pi to the circulatory system 3.

Thanks to this characteristic, it is possible to ensure that any portion of the internal circuits Pi intended to be connected to at least one of the venous or arterial ports Px1, Px2 are previously filled with physiological fluid by connecting it between the physiological fluid supply port φe and the physiological fluid discharge port φs.

The supply port φe can be connected to a first physiological liquid tank, possibly equipped with a debubblizer, and the discharge port φs can be connected to a second physiological liquid recovery tank. These first and second tanks are preferably external to the interface device.

Alternatively, the supply port φe and discharge port φs can be connected to each other via a circulation loop external to the interface device, this loop comprising a circulation pump, a debubblizer and a saline reservoir.

In each of these embodiments, the objective is to supply the interface device with physiological liquid that does not contain bubbles.

Ideally, throughout the transition of the interface device from one of its configurations to another, all portions of the internal circuits Pi are sealed at their ends by rubbing against complementary surfaces inside the interface device. This avoids the communication of device ports during a configuration change.

To achieve this closure, as in the example in FIG. 2a, the ends of the portions of internal circuits Pi intended to be connected to one of the venous or arterial ports can be sealed by rubbing against complementary surfaces of a body Cp throughout the passage of the interface device between its first and second given configurations.

In the embodiment presented in FIG. 2a, the portions of internal circuits Pi intended to be connected to one of the venous or arterial ports are formed in cells/sections A2, A3, A4, A5, A6a, A6b, A7 of a drawer T1. After filling a portion of the internal circuit Pi with physiological fluid, this portion is moved by the control mechanism towards the body Cp which closes it until it reaches a predetermined position with respect to the ports of the device it is to put into fluid communication.

At the moment of fluid communication between a portion of the internal circuit Pi and a venous or arterial port, the physiological liquid in this portion of the internal circuit Pi passes to the port to which it is connected without risk of gas/air introduction.

The operation of the device will now be explained in reference to FIGS. 3a and 3b.

By convention, each of the cells A1 to A8 and B1, B2 of the drawers T1, T2 have several references each formed by a one-digit letter followed by the character "'". Each of these references in the cell corresponds to the port identified by a "P" and followed by the same letter and the same number.

When a reference with the character "'" is in front of an "X", it means that this cell is arranged to prevent the passage of fluid to the corresponding reference port.

For example, on cell A1 of drawer T1, references B3', B1x', R1', R2', B4' and B2x' are each opposite "X" which implies that when this cell A1 is in its operating position, then all the corresponding ports Pb3, Pb1x, Pr1, Pr2, Pb4 and Pb2x are closed.

On the other hand, when a reference of a cell is located along a line drawn in this cell then it means that an internal circuit is provided to connect between them two of the device ports when this cell is in the position of use.

The ports connected by this internal circuit are those designated by the references located along this line.

Thus, on cell A1, along the line the references M1', M2' are seen, which indicates that when this cell A1 is in its position of use then the ports Pm1 and Pm2 of the device are put in fluidic relationship with each other.

Another example, when cells A2 and B1 are in their respective positions of use (configuration A2B1) then a line extending through each of cells A2 and B1 is seen, with the references M1' and M2' placed along this line. This means that when these cells A2 and B1 are in their operating positions then the ports Pm1 and Pm2 are connected to each other via this internal circuit which passes through cells A2, B1.

A first step in using system 0 is to mechanically connect the ports of interface device 1 to the hemodialysis machine 2, tubes X1, X2 and at least some of the different devices B1x, B2x, B3, B4, R1, R2 to be used, and to place device 1 in its first configuration (step 1).

The device R1 can be a specific port of the hemodialysis machine 2 used only when returning blood at the end of the hemodialysis session or possibly a bag of blood or medication to be injected at the end of the hemodialysis session.

In this first configuration A1B1 (step 1) the hemodialysis machine 2 is operated to circulate liquid between ports Pm1 and Pm2.

The liquid then circulates in a loop between machine 2 and interface device 1 via the debubblizer D, which evacuates the bubbles from the liquid.

Machine 2 performs this circulation until it detects, or an operator detects, that the machine circuit and interface device contain only liquid.

In an embodiment such as that shown in FIG. 2c or 1c, where the first and second drawers T1 and T2 are very far apart, means can be provided to fill the circuit connecting these drawers with liquid. To this end, the first and second drawers have cells A2 and B1 respectively which, when in the operating position, allow fluid to flow between ports Pm1 and Pm2 via a circuit passing through these cells A2, B1 (see example in FIG. 2c and step 2 in FIG. 3/configuration A2B1).

After filling the interface device 1 and the internal circuit of the hemodialysis machine 2 with liquid, the control mechanism (e.g. a motor or electromagnet) is activated to move the interface device into its unlocking configuration A3B2 (step 3) which allows the operation of the venous and arterial suction syringes B1x and B2x. The locking fluid contained in the tubes X1, X2 is then sucked in. If necessary, the syringes can be driven and controlled by the control unit of the hemodialysis machine.

Once the tubes X1, X2 have been discharged of the locking fluid, the control mechanism is controlled so that the interface device switches to its second configuration A4B2 (step 4). In this configuration the arterial tube X2 is connected to the input port M2 and the venous tube X1 is connected to the output port M1. The patient's blood can then circulate in a loop through the hemodialysis machine 2 for dialysis.

Once hemodialysis is completed, and as an option, it may be desirable to return a particular liquid to the patient. In this case, this liquid can be supplied via a restitution start port Pr1 that belongs to the interface device. This port Pr1 can be connected to a specific blood outlet R1 of the hemodialysis machine or to a blood or drug bag R1.

To this end, the control mechanism is activated so that the interface device switches to the restitution start configuration A5B2 (step 5). In this configuration, the port Pr1 is connected to the port Pm2 and the venous tube X1 is connected to the output port M1. The particular liquid to be returned then passes successively through the port Pr1, the port Pm2, the input port M2, the hemodialysis machine, the output port M1, the port Pmt and finally reaches the venous tube X1.

It should be noted that this step may be optional and that the system according to the invention may not have a device R1, port Pr1, and may never go through the configuration A5B2. In this case, cell A4 could be deleted from drawer T1.

Once this step 5 is completed or, if there is no step 5, once step 4 is completed, the control mechanism is activated so that interface device 1 switches to the venous delivery configuration A6aB2 (step 6A) which allows:

the closure of the arterial port Px2/arterial tube X2; and
connecting the peripheral device R2 to the machine input port M2 via the release port Pr2 and the second port Pmt.

This peripheral device R2 can be a reserve of fluid R2 to be released when the interface device is in its venous release configuration A6aB2.

Typically, the fluid in the reserve R2 is saline used to push the remaining blood in the machine to the venous tube X1.

The detection device 21 can detect the arrival of saline and thus detect the end of the venous restitution operation.

Once this step 6A is complete, the control mechanism is activated so that interface device 1 switches to arterial restitution configuration A6bB2 (step 6B), which allows the closure of the venous port Px1 and first port Pmt and the connection of the peripheral device R2 with the arterial tube X2 via the restitution port Pr2 and the arterial port Px2.

The release fluid contained in the reservoir R2 can then flow through the interface device 1 to drive the blood contained in the arterial tube X2 to the patient.

The restitution operation is completed when a predetermined volume of liquid has been returned to the arterial tube X2.

Once this step 6B is complete, the control mechanism is activated so that interface device 1 switches to the locking configuration A7B2 (step 7), which on the one hand allows the device B3 to communicate with the venous tube X1 via port Pb3 and port Px1 and on the other hand allows the device B4 to communicate with the arterial tube X2 via port Pb4 and port Px2.

In this locking configuration all other ports of the device are closed.

The device B3 is a venous syringe for injecting locking fluid B3 dedicated to injection to port X1 and the device B4 is an arterial syringe for injecting locking fluid B4 dedicated to injection to port X2.

After this injection of the locks, the interface device can either be directly disconnected from the patient and from the hemodialysis machine, or all ports of the interface device can be closed to disconnect it, or the proximal line that connects the interface device to the hemodialysis machine can be drained.

It is this last emptying step that is shown in FIG. 8, with the device then in the emptying configuration A8B1. In this configuration A8B1, ports Px1 and Px2 are isolated and ports Pmt and Pmt are connected so that the fluid between interface device 1 and machine 2 can be removed.

The case where this invention is used to perform hemodialysis on patients permanently equipped with X1 and X2 tubes will now be presented.

Figure 1D:
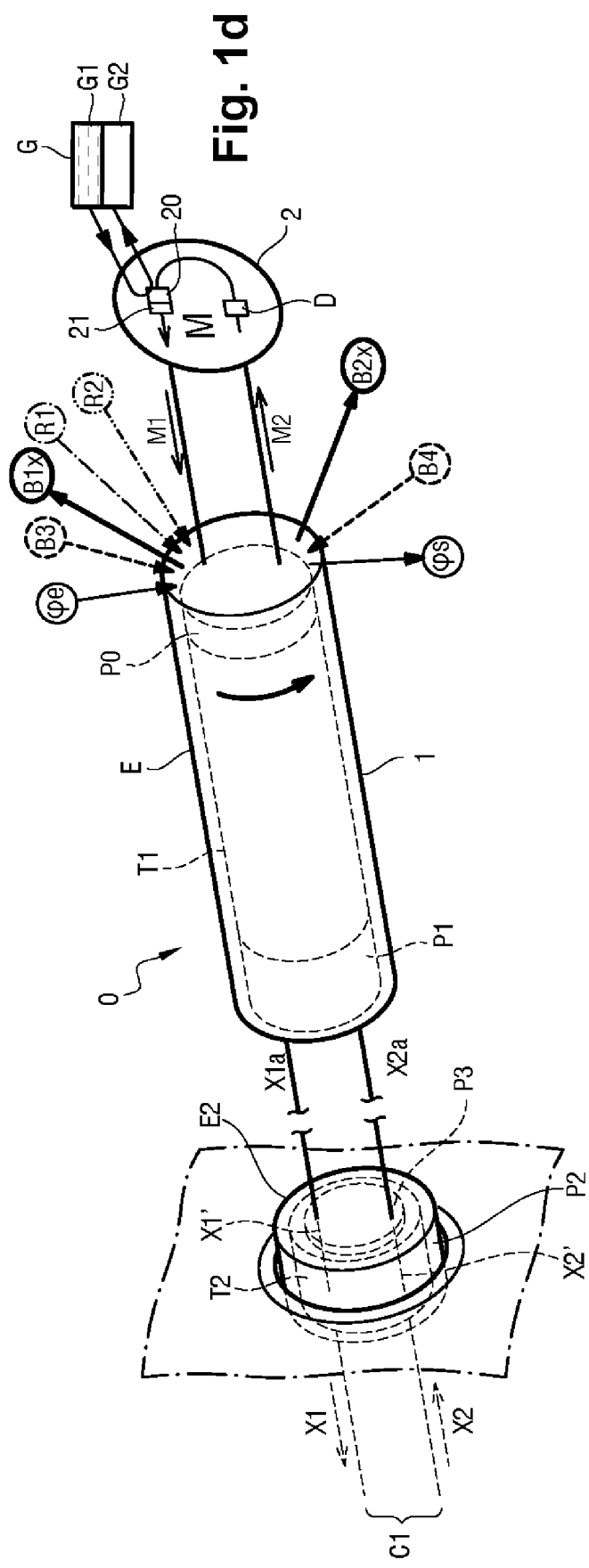
FIG. 1d illustrates a system identical to that of FIG. 1c, the only difference being that the second enclosure E2 is integrated into a patient's tissue, for example it can be implanted subcutaneously or transcutaneously as in FIG. 1d, this second enclosure E2 having possibly an integrated osteo external surface.

In this case, with reference to the embodiment of FIG. 1d, it is possible to provide that device 1 includes an osteointegrated abutment with a connector implanted on the patient at which ends each of the tubes X1 and X2.

The venous port Px1 of the interface device 2 is connected to the venous tube X1 via an intermediate venous tube X1a whose first end is connected to the venous port Px1 and whose second end ends in a second removable connector of the patient.

The arterial port Px2 of the interface device 2 is connected to the arterial tube X2 via an intermediate arterial tube X2a, one end of which is connected to the arterial port Px2 and a second end of which is connected to the patient's second removable connector.

The connector implanted on the patient and the second removable connector of the patient are arranged to be able to be assembled with each other in a reversible manner and in such a way that when they are assembled with each other the venous tube X1 is sealed by the intermediate venous tube X1a and the arterial tube X2 is sealed by the intermediate arterial tube X2a.

The connector implanted on the patient has valves arranged to allow fluid to flow between the implanted tubes X1, X2 and the intermediate tubes X1a, X2a when the implanted connector is assembled with a second removable connector and a movable valve control, between a valve closing configuration and a valve opening configuration, is in its valve opening configuration.

Note that the valve control can be moved between its valve closing configuration and valve opening configuration as long as the implanted connector is assembled with the second removable connector. The valve control is preferably provided so that in the event of disassembly of the second removable connector opposite the implanted connector, the valve control automatically moves from its valve opening configuration to its valve closing configuration. This prevents the implanted tubes X1, X2 from opening directly outside the patient.

To conclude, the interface device 1 according to the invention and the hemodialysis system 0 in which it is integrated allow, in their different embodiments, to:
- perform several functions necessary for the patient's hemodialysis;
- reduce the risk of infection of the patient during hemodialysis by limiting manual operations of connection or disconnection of venous and arterial tubes to the venous and arterial ports Px1, Px2 and the machine exit and entry ports M1, M2 with respect to the first and second ports Pm1, Pmt of the interface device (all fluid isolation or connection operations with devices necessary for hemodialysis are possible without having to disconnect a single port from the device with respect to one of these devices);
- limit the risk of handling errors during the hemodialysis procedure 0;
- limit the risk of contamination by reducing the need for port handling;
- reduce the intervention time of the nursing staff during hemodialysis;
- reduce the preparation and ending time of the hemodialysis session (saving about 10% of the total duration of a hemodialysis session for the patient and caregivers).

This interface device 1 is also compatible with different types of hemodialysis machine 2 without the need to modify them.

The invention claimed is:

1. An interface device between a hemodialysis machine and a venous tube intended to be connected to a patient's circulatory system containing blood for transferring the blood from the hemodialysis machine to the circulatory system, the interface device comprising:
a first port adapted to be connected to an output port of the hemodialysis machine;
a venous port to inject the blood into the venous tube;
the interface device being adapted to selectively adopt a first configuration in which the blood is restricted from passing between the first port and the venous port and a second configuration in which the first port is connected to the venous port to allow the blood to pass from the first port to the venous port, characterized in that the interface device is also adapted to form an interface between the hemodialysis machine and an arterial tube for connection to said patient's circulatory system to transfer the blood from the circulatory system to the hemodialysis machine, said interface device also comprising:
a second port adapted to be connected to an input port of the hemodialysis machine;
an arterial port for receiving the blood from the patient via the arterial tube, the interface device being further adapted to restrict the blood from passing between the second port and the arterial port when the interface device is in the first configuration and to allow the passage of the blood between the second port and the arterial port when the interface device is in the second configuration,
wherein the interface device also comprises a third port, the interface device being adapted to selectively adopt an unlocking configuration distinct from said first and second configurations, in the unlocking configuration the third port being connected to only one of said venous port or arterial port while the first port and the second port are respectively isolated from the venous port and the arterial port, wherein the venous port and arterial port are isolated from each other.

2. The interface device according to claim 1, further adapted to connect, via an internal circuit to the interface device, the first port and the second port when the interface device is in the first configuration and to prohibit communication between the first port and the second port via the internal circuit when the interface device is in the second configuration.

3. The interface device according to claim 1, also comprising a fourth port, the interface device being such that when in the its unlocking configuration, the fourth port is connected to one of said venous port and arterial port which is not connected to said third port and is isolated from the first, second and third ports.

4. The interface device according to claim 1, also comprising a fifth port, the interface device being adapted to selectively adopt a locking configuration distinct from said first, second and unlocking configurations, in the locking configuration, the fifth port being connected to said venous port while the first port, the second port, the third port, the venous port and the arterial port are isolated from each other.

5. The interface device according to claim 4, also comprising a sixth port, the interface device being adapted so that in the locking configuration, the sixth port is connected to said arterial port while being isolated from the first port, the second port, the third port, the fourth port, the fifth port, and the venous port.

6. The interface device according to claim 1, also including a restitution port, the interface device being adapted to selectively adopt a venous restitution configuration distinct from the first and second configurations of the interface device, wherein in the venous restitution configuration, the restitution port is connected to said second port to be able to inject a restitution fluid into the hemodialysis machine, the first port is connected to said venous port and isolated from each of the second port, the arterial port and the restitution port, and the arterial port is at least isolated from the venous port, the first port and the second port.

7. The interface device according to claim 6, adapted to selectively adopt an arterial restitution configuration distinct from the first, second and venous restitution configurations of the interface device, wherein in the arterial restitution configuration, the restitution port is connected to said arterial port to be able to inject a restitution fluid into the arterial tube, and the venous port of the interface device is isolated from each of the first port, the second port, the restitution port and the arterial port.

8. The interface device according to claim 6, wherein said interface device is adapted so that, when in the first configuration, the return port is connected to at least one of said first port and second port.

9. The interface device according to claim 1, wherein said interface device comprises a control mechanism arranged to move in a first direction with respect to an enclosure of the interface device, wherein movement of the control mechanism is the first direction controls a transition of the interface device from the first configuration to the second configuration.

10. The interface device according to claim 1, wherein said interface device includes a physiological liquid supply port to an inner area of the interface device and a physiological liquid discharge port outside the inner area of the interface device, the interface device comprising a plurality of internal circuit portions to the interface device, each of the internal circuit portions being arranged to be selectively connected either between the physiological liquid supply port and the physiological liquid discharge port, or connected to at least one of said venous or arterial ports.

11. A hemodialysis system comprising:
the interface device according to claim 1; and
the hemodialysis machine, the first port of the interface device being detachably connected to the out-put port of the hemodialysis machine and the second port of the interface device being detachably connected to the input port of the hemodialysis machine, the hemodialysis machine having a pump arranged to circulate fluids from the inlet port to the outlet port, the hemodialysis system also comprising a venous tube and an arterial tube, the venous tube being connected to the venous port of the interface device, the venous tube being intended to be connected to the circulatory system of the patient to transfer, via the interface device, the blood from the hemodialysis machine to the circulatory system, the arterial tube being connected to the arterial port of the interface device, the arterial tube being intended to be connected to said circulatory system of the patient to transfer, via the interface device, the blood from the circulatory system to the hemodialysis machine.

12. The hemodialysis system according to claim 11, wherein the system comprises a venous syringe for aspirating locking fluid from the venous tube, the venous syringe being connected to the third port to be able to draw the locking fluid from the venous tube when the interface device is in said unlocking configuration with the third port connected to the venous port.

13. The hemodialysis system according to claim 12, also comprising a fourth port, the interface device being such that when in the unlocking configuration, the fourth port is connected to said arterial port which is not connected to said third port and isolated from the first, second and third ports, wherein the system comprises an arterial syringe for aspirating locking fluid from the arterial tube, the arterial syringe being connected to the fourth port to be able to draw the locking fluid from the arterial tube connected to the fourth port.

* * * * *